United States Patent [19]

Walker et al.

[11] Patent Number: 4,623,736

[45] Date of Patent: Nov. 18, 1986

[54] ARYLALKANOIC ACID PROCESS IMPROVEMENT

[75] Inventors: Jerry A. Walker; Sanjay I. Amin, both of Oshtemo Township, Kalamazoo County, Mich.

[73] Assignee: The Upjohn Company, Kalamazoo, Mich.

[21] Appl. No.: 396,967

[22] Filed: Jul. 9, 1982

[51] Int. Cl.$^4$ .................... C07D 319/06; C07C 69/76
[52] U.S. Cl. .................... 549/369; 568/335; 560/105
[58] Field of Search .............. 560/105; 549/369; 568/335

[56] References Cited

FOREIGN PATENT DOCUMENTS 0034871 9/1981 European Pat. Off. .
0035305 9/1981 European Pat. Off. .

*Primary Examiner*—Paul J. Killos
*Attorney, Agent, or Firm*—John T. Reynolds

[57] ABSTRACT

In preparing arylalkanoic acids, e.g. ibuprofen or naproxen, via the conversion of the selected $\alpha$-haloketal derivative of a 1-haloethyl aryl ketone to the haloalkyl ester of the arylalkanoic acid using a zinc salt catalyst the improvement comprising reacting a ring-substituted 6-membered ring ketal of the selected 1-haloethyl $C_6$–$C_{12}$-aryl ketone with a soluble zinc carboxylate salt to form the corresponding 3-haloalkyl arylalkanoic acid ester. The ester is converted to the alkali metal salt of the acid with base in an aqueous/water insoluble organic liquid mixture and the crude salt is converted to the corresponding acid in an aqueous/water insoluble solvent mixture for the acid, the organic solution of the acid is washed with a pH 7.0 to 8.0 buffer solution, and the arylalkanoic acid product is separated from the mother liquor which mother liquor is recycled to the alkali metal arylalkanoate salt forming step of the process to accumulate and recover the arylalkanoic acid values which remained in the mother liquor.

8 Claims, No Drawings

ARYLALKANOIC ACID PROCESS IMPROVEMENT

INTRODUCTION

This invention relates to a process for preparing arylalkanoate esters and the arylalkanoic acids therefrom. More particularly, this invention provides an improved process for preparing arylalkanoate esters and acids therefrom from ketal derivatives of 1-haloalkyl aryl ketones using zinc carboxylate salt catalysts.

BACKGROUND OF THE INVENTION

Published European Patent Application No. 0,034,871 disclosed that esters of alkanoic acids can be prepared via rearrangement of $\alpha$-haloketals in the presence of a Lewis acid such as a zinc salt. The process is described therein in terms of the preparation of esters of a variety of useful alkanoic acids.

General precedents for the transformation of $\alpha$-haloketones to esters are published, e.g., in the following literature.

Treatment of $\alpha$-bromoisobutyrophenone with silver nitrate in refluxing ethanol was reported to give a 40% yield of $\alpha,\alpha$-dimethylphenylacetic acid: A. C. Cope and E. S. Graham, *J. Amer. Chem. Soc.*, 73, 4702 (1951), and D. J. Paslo and J. P. Sevenair, *J. Amer. Chem. Soc.*, 93, 711 (1970). A very recent modification using silver (I) on an $\alpha$-haloketone was reported by C. Giordano, et al., *Tetrahedron Letters*, 1385 (1982). Also, $\alpha$-halocyclobutanone ketals are known to thermally rearrange to cyclopropanecarboxylates, J. Salaun and J. M. Conia, *Tetrahedron Letters* (1968), p. 4545. However, the use of silver salt catalysts dictates against the commercial use of such chemistry for the production of arylalkanoic acids and that prior art does not disclose procedures for preparing high yields of the desired ester intermediates. Process research studies continue to discover more efficient and less costly methods to prepare a variety of commercially significant arylalkanoic acids which have varied practical uses.

OBJECTS OF THE INVENTION

It is an object of this invention to provide an improved process for preparing arylalkanoate esters, particularly 2-arylalkanoate esters, which are useful as intermediates to make commercially useful arylalkanoic acids, and salts thereof.

It is a more specific object of this invention to provide economically significant improvements to a known process for preparing 2-arylalkanoate esters, and the acids therefrom, involving the rearrangement of a ketal derivative of a 1-haloalkyl aryl ketone in the presence of zinc salt catalysts.

Other objects, aspects and advantages of this invention will be apparent from reading the remaining specification and the claims which follow.

SUMMARY OF THE INVENTION

Briefly, by this invention we have discovered that in a process for preparing arylalkanoic acids via transformation of a ketal derivative of a 1-haloalkyl aryl ketone to the corresponding haloalkyl 2-arylalkanoate ester, and conversion of the ester to arylalkanoate salt, and conversion of the salt to the desired arylalkanoic acid, the end product yields of the desired arylalkanoic acid can be increased and the quality thereof upgraded. The overall process is made simpler and by-product formation and impurity carrythrough is eliminated or minimized by reacting (1) and alicyclic glycol-derived substituted 1,3-dioxane ketal derivative of the selected 1-haloalkyl arylketone with (2) a zinc carboxylate salt which zinc salt is soluble in the ketal (I) reaction mixture at a temperature at which the reaction proceeds, usually at about 100° C. to about 170° C. for a time sufficient to effect conversion of the ketal to the halogenated ester of the arylalkanoic acid. The haloalkyl ester is converted to the alkali metal salt of the acid with an alkali metal base in an aqueous/water insoluble organic liquid mixture and the arylalkanoate salt is separated. The crude salt is converted to the arylalkanoic acid in an aqueous/water insoluble organic liquid solvent for the arylalkanoic acid, the organic solvent solution of the acid is washed with a pH 7.0 to 8.0 buffer solution, and the arylalkanoic acid product is separated from a solution thereof in the organic liquid solvent, and the residual solvent mother liquor, still containing some dissolved arylalkanoic acid therein, is recycled to the earlier salt formation stage of the process to further enhance the overall yield of the aryalkanoic acids.

DETAILED DESCRIPTION OF THE INVENTION

More specifically, we have discovered that a number of problems inherent in designing a commercial scale process for preparing various valuable arylalkanoic acid drugs and other useful compounds from ketal derivatives of 1-haloalkyl aryl ketones and zinc salt catalysis can be eliminated or minimized by (a) contacting and reacting a substituted alicyclic glycol derived 6-membered ketal derivative of a 1-haloalkyl aryl ketone of Formula I, wherein Ar is an aromatic ring containing a radical having from 6 to about 12 carbon atoms in which an aryl ring carbon atom of the Ar moiety is bonded to the C-2 ketal carbon atom;

$R^1$ is hydrogen, $C_1$ to $C_4$-alkyl or phenyl;

each of $R^2$ and $R^3$ is hydrogen, $C_1$ to $C_4$-alkyl or phenyl;

$R^4$ is hydrogen, $C_1$ to $C_4$-alkyl or phenyl, such that the (1)$C_1$ to $C_4$-alkyl substituents in the $R^1$, $R^2$, $R^3$ or $R^4$ positions are essentially linear alkyl group and (2) the resulting ketal compound (I) or mixtures thereof is liquid at reaction temperatures of 100° to 200° C.

X is chlorine, bromine or iodine; and $R^5$ is $C_1$ to $C_3$-alkyl with a catalytic amount of a zinc carboxylic acid salt which zinc salt is soluble in alpha-halo ketal (I) reaction mixture, at a temperature of from the exothermic reaction temperature of the mixture, usually about 100° C. to about 200° C., for a time sufficient to effect conversion of the ketal to a halogenated alkyl ester having the formula selected from the group consisting of Formulas II and III, wherein Ar, $R^1$, $R^2$, $R^3$, $R^4$ and $R^5$ are as defined herein. The particular ester formed (II or III) depends on how the ketal ring opens in the rearrangement step.

The preferred $\alpha$-haloketal reactants are those which contain one or two carbon containing substituents in the $R^1$, $R^2$, $R^3$ and $R^4$ positions, although ketal compounds having any combination of substituents in the $R^1$, $R^2$, $R^3$ and $R^4$ positions could be used. The preferred ketals would be those derived, e.g., from glycols such as 1,3-butanediol, 2-methyl-1,3-butanediol, 2,2-dimethyl-1,3-propanediol, 2-phenyl-1,3-propanediol, 2-phenyl-1,3- butanediol, and the like. Other glycols such as 3-methyl-2,4-pentanediol could also be used to make the α-halo-1,3-dioxane type ketal for use in the process of this invention.

The operation of this ketal to ester rearrangement takes place in the context of an overall process for preparing the desired arylalkanoic acid from the aromatic or Ar-starting material in four steps which can briefly be referred to as the (a) ketalization of the starting Ar-compound (ketone), (b) ketal transformation to the haloalkyl ester, (c) salt formation, and (d) acid formation steps. In our improved sequence of the above steps of operating this process, we first react the α-haloacyl aromatic compound of Formula IV wherein Ar is a residue of the ketone derivative of the selected aromatic base compound starting material, X is chlorine, bromine or iodine, but preferably chlorine or bromine, and $R^5$ is $C_1$ to $C_3$-alkyl, with the defined 1,3-glycol of Formula V in an organic liquid diluent such as hexane, heptane, toluene, xylene or chlorobenzene, or mixtures thereof, but preferably heptane or toluene, in the presence of an acid catalyst such as sulfuric, hydrochloric, methanesulfonic or p-toluenesulfonic acid, to form the desired substituted alicyclic 6-membered ring ketal derivative (I) of the selected 1-haloalkyl aryl ketone above.

Other methods of 60-haloketal formation known in the art can be used.

While the zinc alkanoate salt catalyst can be added to the ketal containing reaction mixture after the ketalization reaction is complete, the excess glycol reactant and the acid catalyst must be removed from the ketal intermediate, e.g., by aqueous extraction or aqueous bicarbonate solution extraction or by distillation of the ketal formation reaction mixture under reduced pressure, to ensure good reaction rates in the ketal rearrangement reaction which is to follow.

The zinc alkanoate salt catalyst is preferably added to the α-haloketal after the excess glycol and the acid catalyst have been removed therefrom.

Examples of zinc carboxylic acid salts which can be used include zinc $C_3$ to $C_{20}$-alkanoates such as zinc propionate, n-butyrate, isobutyrate, valerate, hexanoate, heptanoate, octanoate, nonanoate, dodecanoate, undecanoate, neodecanoate, tridecanoate, palmatate, stearate, and the like, in any of their straight or branched chain alkanoic acid form, as well as some of the zinc aromatic acid salts such as zinc benzoate and the like. Particularly preferred by us are zinc $C_8$ to $C_{16}$-alkanoate salts. More particularly preferred is zinc 2-ethylhexanoate (a zinc octanoate salt) and various commercially available mixture forms of that salt such as Zinc HEX-CEM ® (a product of Mooney Chemical, Inc., Cleveland, Ohio) which is available in various zinc 2-ethylhexanoate, percent by weight concentrations, such as 18 or 22 percent w/w strength in their commercial compositions.

The transformation or conversion of the α-halo-ketal (I) to the haloalkyl arylalkanoate ester in the presence of the zinc carboxylate salt which is soluble at the reaction temperaure range of from about 100° to 200° C., preferably 130° to 150° C., can take place in the same reaction vessel as the ketal formation vessel but this ester formation reaction takes place, according to this invention, in an essentially solvent-free liquid or neat mixture form. Temperatures below 100° C. can be used but such temperature requires an inordinate amount of time for economical operation of the process. Temperatures above 170° C. are not necessary. Times up to 10 hours may be needed with some ketal starting materials to complete the reaction. However, with reaction temperatures being maintained at about 130° to 150° C. reaction times of less than 5 hours, and with some combinations of ketal (I) and zinc carboxylte catalyst concentrations, reaction times of less than 3 hours can be sufficient to convert the bulk of the ketal (I) to the haloalkyl arylalkanoate ester intermediate.

Zinc acetate, a solid, can be used to convert α-halo-ketals to these esters, but the yields therewith are lower on average and the reaction times are longer than with the more soluble higher zinc carboxylate salt catalysts. The zinc carboxylate salts can be used in any catalytic amount ranging from mole to mole ratios, based on the molar concentration of the ketal (I) down to about 1 mole percent of the zinc carboxylate salt, based on the molar concentration of the ketal (I) in the reaction vessel. Concentrations less than about 1 percent of the zinc carboxylate salt can be used, but at these lower concentrations the reaction takes longer times. Generally, we prefer to use from about 1 to about 10 mole percent, more preferably 1 to 2.5 mole percent, of the zinc carboxylate salt, based upon the molar concentration of the ketal (I) in the reaction vessel, at the preferred temperature of 130° to 150° C.

Conducting this ketal (I) rearrangement step essentially neat (without solvent) minimizes problems associated with high heat input necessary to heat the reaction mixture to the preferred reaction temperatures. Use of the soluble zinc carboxylate salts reduces the amount (mole percent) of zinc carboxylate catalyst needed in the mixture, or the need for any co-solvent, which is often needed to make zinc chloride an efficient catalyst in these mixtures. The use of these soluble zinc carboxylate catalysts permits operation of the ketal (I) rearrangement step without the required use of a higher boiling solvent while minimizing the increase of difficult to remove by-product formation in the product. As we studied the catalytic efficiencies of various forms of zinc in this rearrangement, it was found that at temperatures of 130°–150° C., in the absence of solvent a number of zinc carboxylates were very effective catalysts for converting ketal (I) to ester intermediate products. Zinc chloride can not be used effectively in the absence of a solvent or solvent mixture.

A major advantage of conducting the ketal to ester rearrangement step of the process with soluble form zinc alkanoate (zinc carboxylate) catalysts is that with these catalysts the ketal/zinc carboxylate catalyst mixture is homogeneous, unlike the situation when zinc chloride is used as the catalyst. When zinc chloride is used as the catalyst, a variety of mass transfer problems are evident. Zinc chloride is a solid. In zinc chloride catalyzed reactions the rate of reaction is highly dependent upon the temperaure, degree of agitation, form of the catalyst, e.g., particle size, shape, pasty mass, etc., and the scale of the reaction. Also, with zinc chloride-type catalysts, variations in the rate of reaction from run to run are typical and on scale-up reaction rates change depending upon the variables indicated above. Moreover, with zinc chloride, the catalyst is initially a crystalline solid which is free flowing. As the reaction proceeds the catalyst appears to form an unknown sticky, pasty agglomerate or mass[1] which sticks to the reaction vessel wall, thus reducing the specific area of catalyst surface available to promote the ketal to ester rearrangement reaction.

¹The interaction of the zinc chloride with the ketal reactant causes this physical form phenomenon. With the zinc carboxylate soluble salt catalysts used according to this invention, the kinetics of the ketal to ester rearrangement are more consistent and better behaved and much less sensitive to scale-up difficulties, temperature and degree of agitation differences, and the like.

Conversion yields of ketal (I) to ester by the soluble zinc carboxylate salt catalyst process of this invention are very high with little hydrolysis or by-product formation.

We have found that cyclic 1,3-dioxane type of ketal reactants (I) are preferred because they can be prepared directly from the haloalkyl aryl ketones using the substituted glycols in high yields at lower cost. Simple ketals, e.g., the dimethyl ketal, cannot be readily made by this process. In such cases, halogenation of the simple (e.g., dimethyl) ketal is generally required, and such is not as economical.

Of the cyclic ketals, the ethylene ketal (forming a 5-membered dioxolane ring) is most common and is recommended in the European Patent Application No. 0,034,871. We have found that the $\alpha$-halo ethylene ketal has more limited utility in this reaction due to unavoidable, undesired formation of an unsaturated, cyclic by-product, which thus lowers the theoretical and practical yields of the desired end product. In contrast, we have found that the 6-membered ketals (1,3-dioxane) used in the process of this invention do not form undesired by-products (as does the ethylene ketal) and, also, the rate of reaction is much faster (e.g., 3 to 5 times faster) with the 6-membered ring ketals. These discovered properties allow the operation of the process to use milder conditions and less catalyst than the prior processes. Much higher yields of the desired end product of the process are thus possible.

The preferred zinc $C_8$ to $C_{16}$-alkanoate salts are relatively soluble in hydrocarbon solvents. Of these, zinc 2-ethylhexanoate, (22% Zinc HEX-CEM®, Mooney Chemical Company) is one of the lowest molecular weight liquid salts and most chemically pure materials available. It is obtained as a viscous liquid which is miscible with organic solvents and with the haloketal (I) reactant. Its composition is not pure bivalent zinc dicarboxylate. It is "over based" and appears to be a mixture of bivalent zinc bis(2-ethylhexanoate) and zinc (hydroxide)(2-ethylhexanoate). This material is an excellent catalyst for this ketal (I) to ester conversion. Conversion and reaction times comparable to 2.5 mole percent of zinc chloride in chlorobenzene are obtainable with 1 to 2 mole percent of Zinc HEX-CEM® in the absence of solvent at the same temperature. The ketal (I) conversion reaction, according to this invention, is fairly exothermic. According to the process of this invention, the reaction mixture is homogeneous (liquid only—without added solvent) which minimizes mass transfer effects on the outcome of the reaction, with only low levels of zinc carboxylate catalyst needed in the reaction mixture.

By way of example, in a run for producing ibuprofen from commercial grade isobutylbenzene via the neopentyl glycol ketal of 1-chloroethyl-4-isobutylphenylketone, with 1-2 mole percent of Zinc HEX-CEM® catalyst at 135°-145° C., reaction times of 2 to 5 hours were sufficient to obtain greater than 98 percent conversion of the ketal to the 3-chloro-2,2-dimethylpropyl ibuprofen ester. By-product formation was no greater than conducting the same ketal conversion using zinc chloride in chlorobenzene. The major impurity is the 1-chloroethyl-4-(isobutyl)phenylketone and esters formed from isomeric 2-(isobutylphenyl)-propionic acids derived from impurities in the ketone starting material, which ester impurities are removed in the subsequent processing of the crude ester intermediate product.

Alkali-metal Arylalkanoate Salt Isolation

The crude haloalkyl ester (II) or (III), or mixtures thereof, can be carried directly into the hydrolysis (salt forming) step. The hydrolysis of the haloalkyl ester of the arylalkanoic acid can be carried out directly on the neat, crude ester rearrangement product mixture, or after dilution with an organic solvent such as heptane, by mixing the water immiscible organic liquid mixture of the ester with an aqueous solution of the desired alkali metal base such as, e.g., a 40 to 60% w/w solution of sodium or potassium hydroxide, and then heating the mixture to expedite the ester hydrolysis and alkali metal salt formation. For example, heating of the neat ester or organic solvent/ester mixture with a 1.5 molar excess of 50% sodium hydroxide in water solution, relative to the molar content of the ester intermediate for less than one hour at 90° to 100° C. is generally sufficient to complete the hydrolysis, as can be readily determined by gas liquid chromatography (glc) analysis of samples of the reaction mixture. When the hydrolysis reaction is complete the reaction can be diluted with a small amount of water and a water immiscible organic solvent such as heptane, preferably keeping the temperature of the mixture warm enough to keep the alkali metal arylalkanoate salt in solution until all of the water is added. After water addition is complete, the mixture can be cooled and seeded with good quality alkali metal salt of the arylalkanoic acid, from previous preparations. The resulting slurry can be cooled, say to 0° to 10° C. over a short time, say 2-3 hours, and filtered. The separated alkali metal arylalkanoate salt can be washed with organic solvent such as heptane.

Most of the zinc complexes and associated color are removed by dilution of the ketal to ester reaction mixture with the water immiscible organic liquid, e.g., heptane or equivalent diluting liquid (which precipitates some solids such as zinc complexes) and treatment of the mixture with activated carbon. The dilution of the crude haloalkyl ester intermediate product with heptane and isolation of the alkali metal salt of the arylalkanoic acid from the diluted aqueous base/organic liquid mixture results in the efficient removal or purge of process impurities and allows recycle of filtrates from the final product filtration step to be carried out effectively. The by-product from the salt forming hydrolysis of the haloalkyl esters is the haloalcohol of Formulas VI and VII, wherein X, $R^1$, $R^2$, $R^3$ and $R^4$ are as defined herein. These haloalcohol by-products are less hazardous and more easily handled than are the by-products obtained from other ketals, such as the ethylene ketal which generates 2-haloethanol and/or ethylene oxide, both of which are highly toxic and hazardous to process operating personnel.

The hydrolysis of these haloalkyl esters of arylalkanoic acids is more difficult than a simple ester such as the methyl ester. However, the above hydrolysis procedure (50 percent NaOH solution, 1.5 molar excess, at about 100° C.) either in heptane, chlorobenzene or other equivalent water immiscible organic liquid or neat (no added organic liquid) for 0.5 to 1.0 hour is sufficient for complete hydrolysis of esters II and III.

The soluble zinc carboxylates (e.g., 22 percent Zinc HEX-CEM® brand of zinc bis(2-ethylhexanoate)) present when the ketal (I) rearrangement to the haloalkyl ester step is done in the absence of solvent are practically insoluble in water so that aqueous extraction of the ester product/zinc salt catalyst reaction mixture is not feasible or practical. Treatment of this oily mixture with a filter aid (e.g., Celite®) and dilution with heptane followed by carbon treatment proved effective for removing zinc salts and the color. Hydrolysis of the haloalkyl ester intermediate was carried out by treatment of the ester reaction mixture with the 1.5 equivalent of the strong (e.g., 50% w/v) alkali metal hydroxide solution at about 90° to 100° C. for 0.5 to 1.0 hour. Alternatively, the hydrolysis can be carried out without removal of the catalyst.

Although alkali metal salt of arylalkanoic acid crystallization procedures in the past have sometimes caused difficulties in commercial scale processes because of slow filtration rate of plate-like crystalline materials, we have found that in this process, alkali metal arylalkanoate salt crystallization proceeds extremely well from this process system possibly because of the totally different nature of the impurities and the solvent systems used.

The alkali metal salt of the arylalkanoic acid is obtained by diluting the hydrolysis reaction mixture, on completion of the ester hydrolysis reaction, with about 0.5 ml of water for each milliliter of 50% alkali metal hydroxide solution which was used and with about 6 ml of heptane or hexane, or equivalent water immiscible organic liquid, for each milliliter of alkali metal base solution which had been used in the hydrolysis step, at about 80° to 100° C., preferably at about 90° C. The resulting solution is cooled (and seeded with alkali metal arylalkanoate salt, if desired) and the salt product is allowed to separate or crystallize at about 70° C. The resulting crystalline slurry of salt product is cooled, filtered at about 0° to 10° C. and the filtered crystalline salt is washed with organic liquid such as heptane. The chloroalcohol by-products, the neutral impurities and most of the color are removed in the filtrate. In addition, a substantial upgrading of the alkali metal arylalkanoate product results. Acidic by-products, such as the isomeric acids which derive from the hydrocarbon or other aromatic starting material carry through, e.g., in a Friedel-Crafts reaction, are effectively removed from the desired product by this stage in the process. The loss of the desired arylalkanoic acid, as its salt, is minimal, considering the upgrading of the product that is observed at this point. We have found that the degree of purification of the salt product is controlled to some extent by the concentration of the base, the amount of water used, and the crystallization conditions. The alkali metal salt product need not be dried at this stage but can be carried directly into the acid isolation step.

The crystalline salt is dissolved in water, with stirring, at about 40° C. and, if necessary, decolorized with carbon after pH adjustment to about 8.0 to 9.0, preferably to about 8.5.

The alkali metal salt crystallization isolation procedure is advantageous over solvent extraction isolation procedures because the crystallization procedure is less time consuming and avoids a series of solvent extractions, reaction mixture volumes can be kept low, and a highly selective removal of a number of by-products results with little loss of the desired acid product.

Arylalkanoic Acid Isolation

The alkali metal alkanoate salt is dissolved in water and the solution is acidified to a strong pH (say to pH 1.0 or below) with hydrochloric or sulfuric acid, or equivalent acid, and the resulting arylalkanoic acid is extracted into a water immiscible organic solvent, e.g., hexane or heptane, at 40° to 55° C. The volumes of the organic solvents are kept as low as possible, say 2 to 4 ml of solvent per gram of arylalkanoic acid in the mixture, to maintain as high as possible a concentration of the acid product and to minimize solvent removal requirements later.

The resulting concentrated solution of the arylalkanoic acid can then be washed with an aqueous phosphate buffer solution which has a pH of from about 7.0 to about 8.0, preferably about 7.5, which conditions are effective for removing from the organic solvent solution a number of minor polar impurities or by-products formed in the process.

After separating the aqueous buffer wash solution layer from the organic solvent solution of the product acid, the concentration of the ibuprofen in the solution is adjusted by distillation or addition of solvent and the purified organic solution of the arylalkanoic acid product is cooled to about 35°–40° C. and seeded with crystalline product acid. The temperature of the mixture is maintained during crystallization for about 0.5 to 1 hour to allow crystal development and then the mixture is cooled slowly to 20°–30° C. and then to 0° to −20° C. for isolation of the purified crystalline acid.

Process by-products, which are unrelated to the arylalkanoic acid per se, such as the haloalkanol by-product from the ester hydrolyzation step, some of the liquid alkanoic acid, e.g., 2-ethylhexanoic acid from the catalyst, and bivalent zinc compounds, are efficiently removed to below acceptable levels by the above processing procedures.

The α-haloketals (I) are preferably prepared from α-haloketones. The α-haloketones can be prepared by (i) a Friedel-Crafts reaction of the aromatic hydrocarbon or compound, e.g., isobutylbenzene or 6-methoxynaphthalene, with an α-haloacyl halide, e.g., α-chloropropionyl chloride or α-bromopropionyl bromide, and the like, by methods well known to those skilled in the art, or (ii) by halogenation of the selected $C_6$ to $C_{12}$-aromatic ketone by known methods, and reaction of the $C_6$ to $C_{12}$-aromatic α-haloalkyl ketone with the selected substituted 1,3-glycol to form the α-halo-substituted-1,3-dioxane ketal starting material.

The ketalization step may be carried out according to conventional procedures by means of the selected glycol in the presence of an acid catalyst in an organic liquid which azeotropes out of the reaction mixture with water by-product formed in the reaction of the glycol and the ketone. Suitable organic liquids include benzene, toluene, xylene, chlorobenzene, tetrachloroethane, hexane, heptane, and the like.

The introduction of the halogen atom to the alpha-position of the carbonyl group or ketal group carbon atom may be carried out by means of a conventional halogenating agent, e.g., sulfuryl chloride, phosphorous trichloride or tribromide, cupric chloride, cupric bromide, N-bromosuccinimide, N-chlorophthalimide, pyridine perchloride, pyrrolidone perbromide, or the analogous iodides, but the bromides and especially the chlorides are preferred.

The ketalization and α-halo-ketal rearrangement, as well as the ester hydrolysis step can be carried out in the same reaction vessel, without isolating the intermediate products.

The ketones that are used as starting materials for preparing the alpha-halo-ketal reactants (I) may be prepared according to Friedel-Crafts reaction conditions from $C_6$ to $C_{12}$-substituted or unsubstituted aromatic ring containing compounds with the selected alkanoyl halide or α-haloalkanoyl halide in the presence of aluminum chloride or other Lewis acid catalysts.

Examples of suitable α-haloketones which can be used to make valuable acids therefrom via the improved process of this invention include:
6-methoxy-2-naphthyl 1-chloroethyl ketone,
3-phenoxyphenyl 1-chloroethyl ketone,
4-isobutylphenyl 1-chloroethyl ketone,
3,4-dichlorophenyl 1-chloroethyl ketone,
4-methoxyphenyl 1-chloroethyl ketone,
3'-fluoro-4'-phenylphenyl 1-chloroethyl ketone,
and the corresponding 1-bromoethyl ketones, and the like.

Examples of alpha-halo ketals which can be used in the process of this invention include:
2-(1-bromoethyl)-2-(6'-methoxynaphthyl)-4-methyl-1,3-dioxane,
2-(1-chloroethyl)-2-(6'-methoxynaphthyl)-5,5-dimethyl-1,3-dioxane,
2-(1-chloroethyl)-2-(3-phenoxyphenyl)-4,6-dimethyl-1,3-dioxane,
2-(1-chloroethyl)-2-(4'-isobutylphenyl)-5,5-dimethyl-1,3-dioxane,
2-(1-bromopropyl)-2-(4-methoxyphenyl)-5,5-dimethyl-1,3-dioxane,
2-(1-chloroethyl)-2-(3,4-dichlorophenyl)-4-ethyl-1,3-dioxane,
2-(1-chloroethyl)-2-(3'-fluorobiphenyl)-5-phenyl-1,3-dioxane,
and the like.

Preferred dioxane reactants, for reasons of cost, operability in this process, and yield of product experience are those made from the alpha-chloro ketal derivatives of the selected aromatic ketones using neopentyl glycol (2,2-dimethyl-1,3-propanediol).

The improved process is further illustrated by the following detailed examples, but they are not intended to limit the scope of the claimed process. In these examples, temperatures are in degrees Centigrade unless otherwise indicated, brine cooling means an alcohol/water and glycol/water mixture around the vessel; Be means the Baume acid density method for indicating the concentration of acid used, l means liter volume measure and GLC means gas liquid chromatography analysis.

EXAMPLE 1

Preparation of ibuprofen via chloroketal/zinc carboxylate (a) Preparation of 1-chloroethyl-4-isobutylphenyl ketone Into a glass-lined reactor was charged 18 kg (0.138 kg moles) of an anhydrous aluminum chloride and 22 kg of methylene chloride. The mixture was cooled to −5° C. with brine and to this was added 15 kg (0.118 kg moles) α-chloropropionyl chloride over a one-hour period. After stirring the mixture for 15 minutes, 14.4 kg (0.108 kg moles) of isobutylbenzene was added over a one-hour period maintaining the reactor temperature at 0° to −5° C. The solution was stirred for thirty minutes and reaction completion was judged by gas liquid chromatographic analysis. The resulting solution was added over a one-hour period to a solution of 26.6 kg 20° Be hydrochloric acid and 38.6 l of water pre-cooled to about −10° C. with brine. The quench temperature was maintained at 5±5° C. The aqueous phase was extracted with (1) 14.5 kg of methylene chloride and 12 l of water and (2) 2×7.5 kg of methylene chloride. The combined organic phases were then washed twice with 0.88 kg of sodium bicarbonate in 19.6 l of water, to pH 7–8. The solution was concentrated to an oil and 42 kg of heptane added to the hot oil, maintaining the temperature above 50° C.

GLC of the resulting isolated product showed no isobutylbenzene and 96.85% of the above named chloroketone.

(b) Preparation of the neopentyl ketal of the 1-chloroethyl 4-isobutylphenyl ketone, from Step (a) above The crude chloroketone in heptane from (a) was added to 15.6 kg (0.15 kg moles) of neopentyl glycol and 2 l of water present in a glass-lined reactor. The mixture was heated to 90° C. and 0.318 kg (3.2 moles) of concentrated sulfuric acid was added. The mixture was heated to reflux at 97°–107° C. Water was removed via azeotropic distillation. GLC analysis of an aliquot after 8 hours indicated that the reaction was complete. The reaction mixture was cooled to 20°–25° C. and 1.084 kg (12.9 moles) of sodium bicarbonate and 16 l of water was added. The aqueous phase was extracted with 2.2 kg of heptane. The combined organic phases were washed with 16 l of water. The above-named neopentyl chloroketal product was concentrated under vacuum to a yellow oil (removing heptane) which was used without further purification.

GLC of the product showed 94.3% chloroketal and 0.9% starting chloroketone (I), based on area percent on integration of the GLC.

(c) Preparation of 3-chloro-2,2-dimethylpropyl ester of Ibuprofen

The crude yellow oil ketal from Step (b) above, present in a reactor was heated to 140° C., removing any heptane present in so doing. Then 0.340 kg (0.97 mole) of zinc 2-ethylhexanoate (a liquid form catalyst) dissolved in 1 liter of heptane was added slowly, over one hour, to maintain the temperature of the reaction mixture at about 140° to 150° C. This is a moderately exothermic reaction, so catalyst is added slowly to control the temperature of the mixture to within the 135° to 150° C. Under these conditions the heptane solvent for the catalyst is distilled out of the mixture almost immediately so that the reaction mixture of alpha-haloketal and zinc salt catalyst is essentially a neat or undiluted mixture. GLC analysis of aliquot samples of the reaction mixture indicated that the rearrangement reaction was essentially complete in two hours. The resulting black oil reaction mixture was cooled to 25°±5° C. and 1 kg of a filter aid (Celite ®512)* was added to adsorb the zinc compounds in the mixture. Then 34 kg of heptane was added and after stirring for thirty minutes, the heptane diluted mixture was filtered to remove the solids. The filter cake was washed with 10 kg of heptane and the solution was pumped through a sparkler filter filled with 1 kg of activated carbon (granular, 12×40 mm., Darco)** and 4 kg of a filter aid (Celite ®) and recycled to two hours. The carbon/Celite ® cake in the sparkler filter was rinsed with 17 kg of heptane.

*Celite ® is a tradename of Johns-Mansville Corporation for some silica and perlite products.
**Darco brand of charcoal, ICI., America GLC analysis of the filtrate solution showed that it contained 95.7%, based on area integration, of the 3-chloro-2,2-dimethylpropyl ibuprofen ester and 1.7% of the 1-chloroethyl-4-isobutylphenyl ketone reversion product.

(d) Preparation of Sodium Ibuprofen Salt

The chloroester solution prepared in (c) was heated to reflux at 95°–100° C. and 13 kg of 50% sodium hydroxide in water was added over twenty minutes. The mixture was refluxed for forty minutes at 95±5° C. GLC analysis of an aliquot indicated complete reaction. 6.4 liters of water were slowly added to the mixture, keeping the temperature about 75° C. After water addition was complete, the mixture was cooled to 70° C. and was seeded with 30 g of good quality sodium ibuprofen. The resulting slurry was cooled to 0° C. over two hours. The slurry was stirred at 0° C. for thirty minutes and filtered. The sodium ibuprofen cake was washed wih 60 kg of heptane and dried.

(e) Preparation of Ibuprofen from the Sodium Salt

The sodium salt of ibuprofen prepared in (d) was charged into a glass-lined reactor and slurried in 130 liters of water. The salt was dissolved by heating to 60° and 35.9 kg of heptane was added to the solution. 12.9 kg of 20° Be hydrochloric acid was added, maintaining a temperature of 60° C. to pH 1.3. The aqueous phase was extracted with 12.5 kg of heptane. The combined organic phases were washed twice with a pH 7.5 buffer solution (7.25 liters of 0.1N NaOH and 120 g $KH_2PO_4$ in 8.9 liters of water). The heptane soluton was distilled to 71 liters and cooled to 0° to crystallize the ibuprofen. The ibuprofen was filtered and the cake was washed with 20 liters of heptane. After drying with nitrogen, 18.4 kg of ibuprofen (82.8% from isobutylbenzene) was obtained.

The yield of ibuprofen by this process can further be improved because the mother liquor from which the ibuprofen precipitated still contains ibuprofen (equivalent to 3 to 5% yield) and said mother liquor is recycled back into the process rather than spending the time, effort and energy of getting all of the ibuprofen out of the reaction mixture the first time through the described process.

EXAMPLE 2

Preparation of naproxen

Following the procedure of Example 1, but substituting in part (a) thereof 6-methoxynaphthalene for isobutylbenzene in the reaction with the alpha-chloropropionyl chloride, there is formed 1-chloroethyl 6-methoxy-2-naphthyl ketone. Then, as in part (b) of Example 1, the 1-chloroethyl 6-methoxy-2-naphthyl ketone, in heptane, is reacted with neopentyl glycol to form the neopentyl ketal of the ketone (also named 2-(1-chloroethyl)-2-(6'-methoxynaphthyl)-5,5-dimethyl-1,3-dioxane). In step (c) this alpha-chloroketal is mixed with a solution of zinc 2-ethylhexanoate in heptane, at a temperature of from about 135° to 150° C. to distill the heptane away and to cause the rearrangement of the α-chloroketal to the 3-chloro-2,2-dimethylpropyl ester of 2-(6-methoxy-2-naphthyl)propionic acid. The resulting oil can be cooled, treated with filter aid to adsorb zinc compounds, and diluted with heptane, stirred and filtered. The filtrate can be treated with carbon and filter aid material to remove colored impurities. The chloro-ester solution, so clarified, can be mixed with aqueous base as in part (d) of Example 1 to hydrolyze the ester and to form the sodium 2-(6'-methoxy-2-naphthyl)propionate salt. Then the sodium salt intermediate product can be precipitated from the mixture by dilution with water, cooling, seeding with sodium naproxen [sodium 2-(6'-methoxy-2-naphthyl)propionate] crystals and cooled to 0° to crystallize the sodium naproxen salt from the mixture, which solid salt is filtered and washed with heptane and dried, if desired. Then, as in step (c) of Example 1, the sodium naproxen crystals can be converted to the free naproxen acid [2-(6'-methoxy-2-naphthyl)propionic acid] by dilution with water and heptane, acidified as in part (e) of Example 1, separate the aqueous and organic liquid phases and washing the organic liquid phase with an aqueous buffer solution, and the organic solvent can be distilled to leave as residue the substantially pure naproxen acid, which can be further washed and dried with nitrogen to obtain drug-quality naproxen acid for use in preparing pharmaceutical formulations thereof.

EXAMPLE 3

Rearrangement of 2-(1-chloroethyl)-2-[4-(2-methylpropyl)-phenyl]-5,5-dimethyl-1,3-dioxane to ibuprofen 3-chloro-2,2-dimethylpropyl ester with zinc neodecanoate A mixture of 35.46 g crude ketal and 2.27 g zinc neodecanoate (Ventron) was heated with stirring under nitrogen in a 140° C. oil bath for one hour. On cooling, glc analysis indicated a greater than 99% conversion to the desired ester.

In a similar fashion other zinc carboxylates were used as indicated in the following table:

| Ex. | Catalyst | Mol % | Solvent | Conc. (gm/ml) | Temp. | Time | Conversion |
|---|---|---|---|---|---|---|---|
| 4 | Zn Propionate | 5 | none | | 144° C. | 2 hr | 98.7% |
| 5 | Zn Isovalerate | 2.5 | none | | 143 | 2 | 96.8 |
| 6 | Zn 2-Ethyl hexanoate | 2.5 | none | | 145 | <1 | 100 |
| | | 2.5 | chlorobenzene | (0.7) | 140 | <1 | 99.3 |
| | | | heptane | (0.7) | 110 | >5 | 73.4[a] |
| | | | octane | (1.4) | 135 | 3 | 98.6 |
| 7 | Zn Octanoate | 1.3 | none | | 127 | 2 | 99.1 |
| | $Zn(acac)_2$[c] | 10 | none | | 145 | 7 | 93.5[b] |
| | Zn acetate | 11 | none | | 145 | 4 | 90.2[b] |

-continued

| Ex. | Catalyst | Mol % | Solvent | Conc. (gm/ml) | Temp. | Time | Conversion |
|---|---|---|---|---|---|---|---|
|  | ZnCl$_2$[c] | 2.8 | none |  | 145 | 2 | 87.0[b] |

[a] conversion after 5 hours - not complete
[b] for comparison only
[c] Zn(acac)$_2$ = Zinc bis(2,4-pentandionate)

EXAMPLE 8

Preparation of 4-Butyl-α-methyl benzeneacetic Acid

Following the procedure described in Example 1, n-butylbenzene was converted to 2-chloro-1-[4-n-butyl-phenyl]-1-propanone, which was then converted to 2-(1-chloroethyl)-5,5-dimethyl-2-[4-n-butylphenyl]-1,3-dioxane (the ketal). Treatment of the ketal with 1 mol% Zn 2-ethylhexanoate without solvent at 145° C. for three hours gave 4-n-butyl-α-methylbenzeneacetic acid, 3-chloro-2,2-dimethylpropyl ester which was converted to 4-n-butyl-α-methylbenzene acetic acid in an overall yield of ~80%.

nmr (CDCL$_3$)δ0.90 (t, 3H, J=6H$_z$), 1-1-1.8 (m,4H), 1.45 (d, 3H, J=7H$_z$), 2.55 (t, 2H, J=7.5H$_z$), 3.64 (q, 1H, J=7H$_z$), and 7.13 (AB$_q$, 4H, J=9H$_t$, Δ$\gamma_{AB}$=7.9H$_z$); IR (neat) cm$^{-1}$ 2932, 1709, 1513, 1459, 1413, 1378, 1232, 1073, 932, 862 and 839.

EXAMPLE 9

Preparation of 2-(1-chloroethyl)-4-methyl-2-[4-(2-methylpropyl)-phenyl]-1,3-dioxane A mixture of 40.0 gm crude 2-chloro-1-[4-(2-methyl-propyl)-phenyl]-1-propanone, 80.0 gm 1,3-butanediol, and 3.3 gm p-toluenesulfonic acid monohydrate were heated under vacuum (~25-50 mm Hg) at about 100° C. such that slow distillation proceeded. After six hours, the mixture was cooled to 25° C. and the upper glycol layer was extracted with 2×30 ml hexane. The lower product layer was diluted with 50 ml of saturated NaHCO$_3$ solution and was extracted with 3×30 ml of hexane. The combined hexane fractions were washed with 2×50 ml water and dried over sodium sulfate. Concentration in vacuo gave 50.1 gm of the desired ketal as an amber viscous oil which partially crystallized on standing.

nmr (CDCl$_3$)δ0.90 (d, 6H, J=7H$_z$), 1.19 (d, 3H, J=6H$_z$), 1.33 and 1.40 (d, 3H-total, J=6H$_Z$ and J=6H$_z$), 1.78 (m, 3H), 2.42 (d, 2H, J=7H$_z$), 3.80 (m, 4H), and 7.13 (AB$_q$, 4H, J=9H$_z$, Δ$\gamma_{AB}$=15.6 H$_z$).

FORMULAS

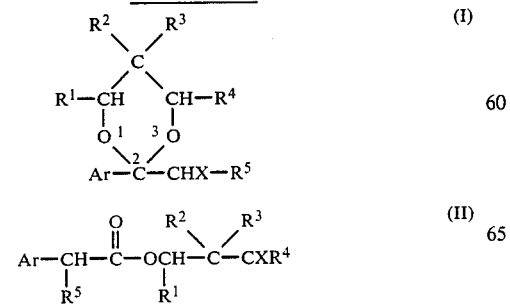

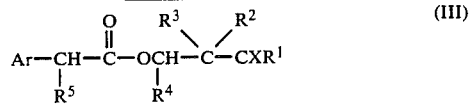

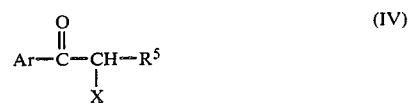

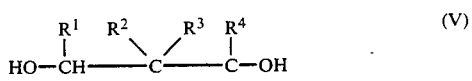

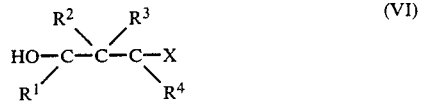

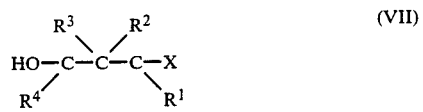

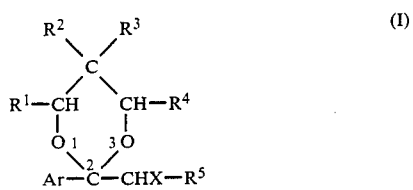

What is claimed is:

1. A process which comprises
contacting and reacting a ring substituted alicyclic glycol derived 6-membered ring ketal derivative of a 1-haloalkyl aryl ketone of formula

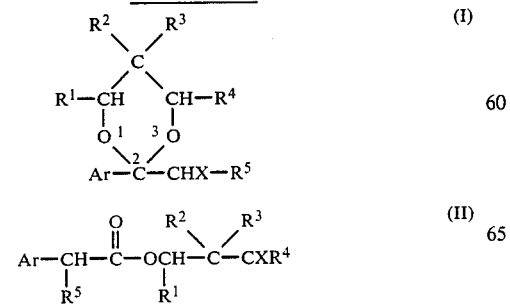

wherein
Ar is an aromatic ring containing radical containing from 6 to 12 carbon atoms in which an aryl ring carbon of the Ar moiety is bonded to the C-2 ketal carbon atom;
R$^1$ is hydrogen, C$_1$ to C$_4$-alkyl or phenyl;
each of R$^2$ and R$^3$ is hydrogen, C$_1$ to C$_4$-alkyl or phenyl;
R$^4$ is hydrogen, C$_1$ to C$_4$-alkyl or phenyl, such that the C$_1$ to C$_4$-substituents in the R$^1$, R$^2$, R$^3$ or R$^4$ positions are essentially linear alkyl groups and the resulting ketal compound (I) is a liquid at temperature of about 100° C. to about 200° C.;
X is chlorine, bromine or iodine; and
R$^5$ is C$_1$ to C$_3$-alkyl, with a catalytic amount of a zinc C$_3$ to C$_{20}$ carboxylic acid salt which zinc salt is soluble in the ketal (I) reaction mixture;
at a temperature ranging from 100° to about 200° C. in an essentially homogeneous, solvent-free liquid form for a time sufficient to effect conversion of the ketal to a halogenated ester having a formula selected from the group consisting of

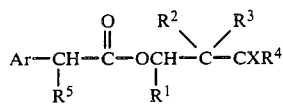  (II)

and

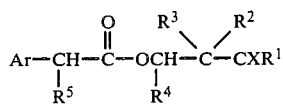  (III)

wherein Ar, $R^1$, $R^2$, $R^3$, $R^4$ and X are as defined above.

2. A process according to claim 1 wherein the ketal (I) is one in which the Ar moiety is a $C_1$ to $C_5$-alkylphenyl group, X is chlorine, and the zinc salt is a zinc $C_8$ to $C_{16}$-alkanoate salt, and the mixture is heated to 130° to 170° C. for a time sufficient to form the haloalkyl 2-($C_1$ to $C_5$-alkylphenyl)propionate ester.

3. A process according to claim 2 wherein the ketal is 2-(1-chloroethyl)-2-(4'-isobutylphenyl)-5,5-dimethyl-1,3-dioxane, the zinc salt is a zinc 2-ethylhexanoate salt, so that there is formed 3-chloro-2,2-dimethylpropyl 2-(4'-isobutylphenyl)propionate ester.

4. A process according to claim 1 wherein the ketal is one in which the Ar moiety is a 6-methoxy-2-naphthyl group, X is chlorine, and the zinc salt is a zinc $C_8$ to $C_{16}$-alkanoate salt, and the mixture is heated for a time sufficient to form a haloalkyl 2-(6'-methoxy-2-naphthyl)propionate ester.

5. A process according to claim 1 which further includes the steps of diluting the haloalkyl arylalkanoate ester with a water immiscible organic liquid solvent, hydrolyzing the organic solvent containing mixture with aqueous alkali metal base to form the alkali metal salt of the arylalkanoic acid, and separating solid alkali metal arylalkanoate salt from the mixture, mixing the solid form alkali metal arylalkanoate salt with water and a water immiscible organic diluent which will dissolve the arylalkanoic acid, acidifying the resulting solution mixture with acid to convert the alkali metal salt to the arylalkanoic which dissolves in the organic liquid, and then separating the arylalkanoic acid product from the organic liquid solvent.

6. A process according to claim 5, applied to the production of ibuprofen, wherein a 3-chloro-2,2-dimethylpropyl ester of ibuprofen is mixed with heptane, the heptane solution of the ibuprofen ester is treated with aqueous alkali metal hydroxide to form the alkali metal ibuprofen salt, the alkali metal ibuprofen salt is crystallized from the mixture, the alkali metal ibuprofen salt is mixed with water and heptane, and the mixture is acidified to convert the alkali metal ibuprofen to ibuprofen acid which dissolves in the heptane, and the ibuprofen is separated from the heptane solution thereof.

7. A process according to claim 5, applied to the product of naproxen, wherein a 3-chloro-2,2-dimethylpropyl ester of naproxen is mixed with heptane, the heptane solution of the naproxen ester is treated with an aqueous alkali metal hydroxide to form the alkali metal naproxen salt, the alkali metal naproxen salt is crystallized from the mixture, the alkali metal naproxen salt is mixed with water and heptane, and the resulting mixture is acidified to convert the alkali metal naproxen salt to naproxen acid, which dissolves in heptane, and the naproxen is separated from the heptane solution thereof.

8. 2-(1-Chloroethyl)-2-[4-(2-methylpropyl)phenyl]-5,5-dimethyl-1,3-dioxane.

* * * * *